United States Patent
Masiz et al.

(10) Patent No.: US 11,865,217 B2
(45) Date of Patent: *Jan. 9, 2024

(54) TRANSDERMAL DRUG DELIVERY SYSTEM

(71) Applicants: BioPhysics Pharma, Inc., Gloucester, MA (US); John J. Masiz, Gloucester, MA (US)

(72) Inventors: John J. Masiz, Topsfield, MA (US); Zhen Zhu, Andover, MA (US)

(73) Assignees: BioPhysics Pharma, Inc., Gloucester, MA (US); John J. Masiz, Gloucester, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/884,727

(22) Filed: Aug. 10, 2022

(65) Prior Publication Data

US 2022/0387343 A1 Dec. 8, 2022

Related U.S. Application Data

(63) Continuation of application No. 16/582,922, filed on Sep. 25, 2019, now Pat. No. 11,446,257.

(Continued)

(51) Int. Cl.
*A61K 47/18* (2017.01)
*A61K 9/70* (2006.01)
(Continued)

(52) U.S. Cl.
CPC .......... *A61K 9/7084* (2013.01); *A61K 9/0014* (2013.01); *A61K 45/06* (2013.01); *A61K 47/18* (2013.01)

(58) Field of Classification Search
CPC .................................................... A61K 9/7074
See application file for complete search history.

(56) References Cited

U.S. PATENT DOCUMENTS 3,903,159 A 9/1975 Hughes et al.
5,460,821 A 10/1995 Masiz
(Continued)

FOREIGN PATENT DOCUMENTS

EP 1 621 192 A1 2/2006
EP 2588067 B1 10/2016
(Continued)

OTHER PUBLICATIONS

"Chaotropic agent" Wikipedia Nov. 26, 2019 (Nov. 26, 2019), pp. 1-2, XP055660163, Retrieved from the Internet: URL:https:;;en.wikipedia.orgjwiki/Chaotropic agent, [retrieved on Jan. 21, 2020.
(Continued)

*Primary Examiner* — Benjamin J Packard
(74) *Attorney, Agent, or Firm* — Antoinette G Giugliano; Antoinette G Giugliano PC (57) ABSTRACT

The present invention relates to transdermal delivery systems, methods and kits that include an agent to penetrate the basement membrane, a membrane of the skin previously known to be difficult to penetrate. In particular, the formulation includes a basement membrane disruptor that reversibly denatures the basement membrane of the skin. The formulation of the present invention further includes having at least one penetration agent, at least one vaso-modulator, and at least one active ingredient. In an embodiment, the penetration agent includes a solvent, a lipophilic agent, a hydrophilic agent, wherein the basement membrane disruptor, the vaso-modulator, and the active ingredient pass through the stratum corneum and epidermis. The basement membrane disruptor allows the vaso-modulator and the active ingredient pass through the basement membrane to dermis. The active ingredient, once at the dermis, is delivered locally to the tissue or systemically to the blood stream.

30 Claims, 1 Drawing Sheet

Related U.S. Application Data (60) Provisional application No. 62/737,479, filed on Sep. 27, 2018.

(51) Int. Cl.
*A61K 45/06* (2006.01)
*A61K 9/00* (2006.01)

(56) References Cited

U.S. PATENT DOCUMENTS

| | | |
|---|---|---|
| 5,645,854 A | 7/1997 | Masiz |
| 5,853,751 A | 12/1998 | Masiz |
| 5,922,772 A | 7/1999 | Durant |
| 5,955,507 A | 9/1999 | Durant et al. |
| 6,611,707 B1 | 8/2003 | Prausnitz |
| 6,635,274 B1 | 10/2003 | Masiz et al. |
| 6,914,051 B1 | 7/2005 | Allen |
| 7,169,814 B2 | 1/2007 | Rothbard et al. |
| 7,198,801 B2 | 4/2007 | Carrara et al. |
| 7,351,743 B1 | 4/2008 | Goldin et al. |
| 7,470,433 B2 | 12/2008 | Carrara et al. |
| 7,687,603 B2 | 3/2010 | Zhao et al. |
| 8,309,514 B2 | 11/2012 | Zhao et al. |
| 8,343,486 B2 | 1/2013 | Carter et al. |
| 8,367,122 B2 | 2/2013 | Stephens et al. |
| 8,802,085 B2 | 8/2014 | Carter et al. |
| 9,278,233 B2 | 3/2016 | Carter et al. |
| 9,427,419 B2 | 8/2016 | De La Terro |
| 9,566,256 B2 | 2/2017 | Carter et al. |
| 9,642,912 B2 | 5/2017 | Kisak |
| 9,855,212 B2 | 1/2018 | Cozean et al. |
| 10,322,077 B2 | 6/2019 | Carter et al. |
| 10,624,867 B2 | 4/2020 | Varadi et al. |
| 2002/0004065 A1 | 1/2002 | Kanios |
| 2003/0133969 A1 | 7/2003 | Bergeron |
| 2003/0185788 A1 | 10/2003 | Bothbard et al. |
| 2004/0115135 A1 | 6/2004 | Quay |
| 2006/0062836 A1 | 3/2006 | Carter |
| 2007/0072802 A1 | 3/2007 | Zhao et al. |
| 2007/0078094 A1 | 4/2007 | Zhao et al. |
| 2007/0166361 A1 | 7/2007 | Carrara et al. |
| 2007/0185216 A1 | 8/2007 | Snyder |
| 2008/0319092 A1 | 12/2008 | Singh |
| 2009/0214504 A1 | 8/2009 | Carter et al. |
| 2009/0311200 A1 | 12/2009 | Lambert et al. |
| 2010/0003353 A1 | 1/2010 | Stephens et al. |
| 2010/0076035 A1 | 3/2010 | Carter |
| 2010/0145256 A1 | 6/2010 | Carter et al. |
| 2010/0160210 A1 | 6/2010 | Zhao et al. |
| 2013/0245538 A1 | 9/2013 | Carter et al. |
| 2013/0273019 A1 | 10/2013 | Carter et al. |
| 2014/0199741 A1 | 7/2014 | Carey |
| 2015/0320710 A1 | 11/2015 | Holubec |
| 2016/0058725 A1 | 3/2016 | Carter |
| 2016/0128957 A1 | 5/2016 | Carter et al. |
| 2016/0129116 A1 | 5/2016 | Carter et al. |
| 2016/0213586 A1 | 7/2016 | Carter et al. |
| 2016/0235846 A1 | 8/2016 | Carter et al. |
| 2017/0095433 A1 | 4/2017 | Carter et al. |
| 2017/0232210 A1 | 8/2017 | Boeckl |
| 2017/0239173 A1 | 8/2017 | Obae |
| 2018/0036226 A1 | 2/2018 | Rutolo, Jr. |
| 2018/0319825 A1 | 11/2018 | McKinley et al. |
| 2018/0325851 A1 | 11/2018 | Varadi et al. |
| 2020/0101025 A1 | 4/2020 | Masiz |
| 2021/0259951 A1 | 8/2021 | Masiz |

FOREIGN PATENT DOCUMENTS

| | | |
|---|---|---|
| WO | WO 95/00088 | 1/1995 |
| WO | WO1995020950 A1 | 8/1995 |
| WO | WO1997013482 A1 | 4/1997 |
| WO | WO2003049772 A2 | 6/2003 |
| WO | WO2010034019 A1 | 3/2010 |
| WO | WO2010065922 A2 | 6/2010 |
| WO | WO2018213071 A1 | 11/2018 |
| WO | WO2020069013 A1 | 4/2020 |

OTHER PUBLICATIONS

International Search Report and Written Opinion, PCT application No. PCT/US2019/053000, dated Feb. 3, 2020.
Park, Alice, "Scientists Have Discovered a New Organ in the Human Body. What is the Interstitium?" *Time Magazine*, Mar. 28, 2018 (downloaded Aug. 28, 2019).
International Preliminary Report on Patentability and Written Opinion, PCT application No. PCT/US2019/053000, dated Apr. 8, 2021.
Sethi, Anish, et al., "Moisturizers: The Slipper Road" *Indian J Dermatol* May-Jun. 61(3): 279-287 (2016).
C W Lynde, "Moisturizers: what they are and how they work" Abstract Skin Therapy Lett Dec 6(13): 3-5 (2001) https://pubmed.ncbi.nlm.nih.gov/11813097/ downloaded May 19, 2021.
"Urea" Wikipedia https://en.wikipedia.org/wiki/Urea [retrieved May 19, 2021].
Bennion, Brian J. et al., "The Molecular Basis for the Chemical Denaturation of Proteins by Urea" PNAS 100 (9): 5142-5147 (Apr. 29, 2003).
"Urea-containing cream" Wikipedia https://en.wikipedia.org/wiki/Urea-containing_cream [retrieved May 19, 2021].
"Guanidine" Drugs.com https://www.drugs.com/pro/guanidine.html [retrieved Jan. 21, 2022].
International Search Report and Written Opinion, PCT application No. PCT/US2021/018318, dated Jun. 4, 2021.
Rossano Rocco et al.: "What Are the Proteolytic Enzymes of Honey and What They Do Tell Us? A Fingerprint Analysis by 2-D Zymography of Unifloral Honeys" *PLOS ONE*, vol. 7, No. 11: p. e49164, Nov. 7, 2012.
Juergens U.: "Anti-inflammatory Properties of the Monoterpene 1.8-cineole: Current Evidence for Co-medication in Inflammatory Airway Diseases" Drug Research, vol. 64, No. 12, 15:638-646, May 2014.
PubChem Eucalyptol (Compound), Section 11.2.1First Aid https://pubchem.ncbi.nlm.nih.gov/compound/Eucalyptol#section=First-Aid-Measures [retrieved Nov. 21, 2022].

TRANSDERMAL DRUG DELIVERY SYSTEM

RELATED APPLICATIONS

This application is a continuation of U.S. application Ser. No. 16/582,922, entitled, "Transdermal Drug Delivery System" by John J. Masiz et al., filed Sep. 25, 2019, which claims the benefit of U.S. Provisional Application No. 62/737,479, entitled, "Transdermal Drug Delivery System" by John J. Masiz, filed Sep. 27, 2018.

The entire teachings of the above applications are incorporated herein by reference.

BACKGROUND OF THE INVENTION

The efficient delivery of drugs or active pharmaceutical agents has long been one of the goals of the pharmaceutical community. Oral delivery of medications involves gastrointestinal impact, first pass liver effect, and inter-gut, and drug-to-drug interactions.

Historically, the success of transdermal delivery technologies has often been limited. The first successful class of transdermal technology consisted of the patch. Patch technology is a primitive technology using a band aid like device to hold a drug in contact with the skin. The premise is that with osmosis, the drug will passively penetrate into the skin, through the skin and then migrate into general circulation. Patch technology has generally been somewhat successful in delivering a few compounds that, among other characteristics, have a high log-p value, small Dalton weight, and a linear molecular structure with flexible molecular bonds. Currently, there are only about 15 or so drugs that meet these criteria. These are drug compounds such as nicotine, estrogen, testosterone, scopolamine, fentanyl, diclofenac, etc. At this time, about 90% or more of the pharmacopeia cannot be delivered by patch technology including the newly developed iontophoretic and microneedle patches.

Accordingly, a need exists for transdermal delivery systems and methods that provide delivery of a larger variety of pharmaceutical agents and to do so in effective amounts. Yet a further need exists for an improved transdermal delivery system that provides localized and targeted tissue delivery or general systemic delivery with a faster onset of action. Such an improved transdermal delivery system would also avoid unwanted effects from oral delivery of medications.

SUMMARY OF THE INVENTION

The present invention relates to a formulation for transdermal delivery of an active ingredient to a mammal (e.g., human or animal), wherein the mammal has a body surface that comprises a stratum corneum, an epidermis, a basement membrane, and a dermis. The formulation includes at least one penetration agent (e.g., a solvent, a lipophilic agent, a hydrophilic agent, or a combination thereof), at least one basement membrane disruptor that reversibly denatures the basement membrane; at least one vaso-modulator; and at least one active ingredient. The inventive formulation allows for penetration of the active ingredient to the dermis. In an aspect, the body surface includes skin, mucosal membranes (e.g., vaginal mucosa, anal mucosa, throat mucosa, nasal mucosa, or ocular tissue), nail surfaces (e.g., fingernail surface or toe nail surface) or any combination thereof.

The penetration agent of the present invention, for example, allows the basement membrane disruptor, the vaso-modulator, and the active ingredient to pass through the stratum corneum layer and the epidermis. The penetration agent includes solvents such as one or more nonpolar solvents (e.g., carbon tetrachloride, benzene, diethyl ether, hexane, methylene chloride, toluene and a combination thereof), one or more polar aprotic solvents (e.g., propylene carbonate, acetone, ethyl acetate, acetonitrile, dimethylformamide, and a combination thereof), one or more polar protic solvents (e.g., water, methanol, isopropanol, acetic acid, methanol, ethanol, n-propanol, n-butanol and a combination thereof), one or more limonenes (e.g., D-limonene, L-Limonenes and a combination thereof), and any combination thereof.

The formulation of the present invention includes basement membrane disruptor that allows the vaso-modulator and the active ingredient pass through the basement membrane. Basement membrane disruptors used in the present invention include, for example, one or more chaotropic agents, or one or more other agents that allow for reversibly denaturing and permeability of the basement membrane proteins. Examples of a basement membrane disruptor include guanidine hydrochloride, a guanidine salt, guanidine analogs, guanidine conjugates, or any combination thereof.

The formulation of the present invention includes a vaso-modulator that encompasses a vasodilator or vasoconstrictor. In an embodiment, the vasodilator allows for the active ingredient to be delivered systemically or to local tissue. Examples of vasodilators include amrinone, arginine, bamethan sulphate, bencyclane fumarate, benfurodil hemisuccinate, benzyl nicotinate, buflomedil hydrochloride, buphenine hydrochloride, butalamine hydrochloride, cetiedil citrate, ciclonicate, cinepazide maleate, cyclandelate, di isopropylammonium dichloroacetate, ethyl nicotinate, heproni-cate, hexyl nicotinate, ifenprodil tartrate, inositol nicotinate, isoxsuprine hydrochloride, kallidinogenase, methyl nicotinate, naftidrofuryl oxalate, nicametate citrate, niceritrol, nicoboxil, nicofuranose, nicotinyl alcohol, nicotinyl alcohol tartrate, nitric oxide, nonivamide, oxpentifylline, papaverine, papaveroline, pentifylline, peroxynitrite, pinacidil, pipratecol, propentofyltine, raubasine, suloctidil, teasuprine, thymoxamine hydrochloride, tocopherol nicotinate, tolazoline, papaverine, xanthinol nicotinate, diazoxide, hydralazine, minoxidil, and sodium nitroprusside, clonidine, quanaberz, methyl dopa, alpha adrenoceptor, indoramin, phenoxybenzamine, phentolamine, prazosin, PDE-5 inhibitors, sildenafil, tadalafil, adrenergic neuron blocking agents, bedmidine, debrisoquine, guanethidine, ACE inhibitors, benazepril, captopril, cilazapril, enalapril, fosinopril, lisinopril, perindopril, quinapril, ramipril, ganglion blocking agents, pentolinium, trimetaphan, calcium channel blockers, amlodipine, diltiazem, felodipine, isradipine, nicardipine, nifedipine, nimodipine, verapamil, prostaglandins, prostacyclin, thrombuxane A2, leukotrienes, PGA, PGA1, PGA2, PGE1, PGE2, PGD, PGG, PGH, angiotensin II analogs, saralasin, nitroglycerin, labetalol, thrazide, isosorbide dinitrate, pentaerythritol tetranitrate, digitalis, hydralazine, diazoxide, sodium nitroprusside, and any combination thereof.

In the case in which the vaso-modulator used in the present invention is a vasoconstrictor, the active ingredient is delivered to the dermis. In an embodiment, vasoconstrictors used with the inventive formula of the present invention encompass adenosine triphosphate, amphetamine, antazoline, asymmetric dimethylarginine, cocaine, dopamine, endothelin, ephedrine, epinephrine, ergine, hydroxyamphetamine, isoproterenol, levonordefrin, metaraminol, methamphetamine, methoxamine, methylphenidate, neuropeptide Y, naphazoline, norepinephrine, oxymetazoline, phenylephrine, pseudoephedrine, tetrahydozoline, thromboxane, tramazoline, tyramine, and any combination thereof.

The transdermal delivery formulation or system of the present invention can deliver a wide variety of active ingredients. Active ingredients can be used to treat a number of diseases, disorders, or conditions including musculoskeletal disease, vascular disease, neurological diseases, viral, bacterial or parasitic disease, blood disease, skin disease, autoimmune diseases, organ disease, pain, and others. Accordingly, active ingredients of pharmaceuticals used to treat these diseases can be used in the transdermal delivery system of the present invention. Examples of active ingredients include acetaminophen, acetohydoxamic acid, acetophenazine, acyclovir, albuterol, allopurinol, amiloride, amoxicillin, amphetamine, ampicillin, antisense polymers, atenolol, baclofen, beclomethasone, benfotiamine, betamethasone, budesonide, bumetanide, butorphanol, carbamazepine, carphenazine, celacoxhib, cefuroxime, cephradine, chloramphenicol, chlorothiazide, chlorzoxazone, cinoxacin, clorazepate, cloxacillin, cyclacillin, dapsone, dicloxacillin, diethylstilbestrol, dopamine, doxorubicin, erythropoietin, estradiol, fenoprofen, gabapentin, human growth hormone, hydralazine, hydrochlorothiazide, ibuprofen, indomethacin, insulin, isoproterenol, ketoprofen, levodopa, levothyroxine, meclofenamate, melphalan, metformin methyl salicylate, metronidazole, minoxidil, morphine, nadolol, nalidixic acid, naproxen, nomifensine, norfloxacin, oxaprozin, oxycontin, paramethasone, peptide fragments, perphenazine, phenylpropanolamine, pregabalin, probenecid, quinethazone, ritodrine, scopolamine, serotonin, sildenafil, tadalafil, terbutaline, terfenadine, tocainide, terbinafine, triamterene, riamterine, a sirtuin inhibitor, nicotinamide, AIII, coumarin, sirtinol, alpha-NAD, carbamido-NAD, trichostatin A, suramin sodium, apicidin, BML-210, BML-266, depudecin, HC Toxin, ITSA1, nullscript, phenylbutyrate, sodium, scriptaid, splitomicin, suberoyl bis-hydroxamic acid, a sirtuin activators, resveratrol, isonicotinamide, butein, luteolin, plant extract, and any combination thereof.

In another aspect of the invention, the transdermal delivery system also includes transpiration barrier, wherein the transpiration barrier can be a chemical barrier or a physical barrier.

The present invention relates to methods for transdermal delivery of a formulation having an active ingredient to a mammal, wherein the mammal has a body surface that includes a stratum corneum, an epidermis, a basement membrane, and a dermis. The steps of the method include applying the formulation, described herein, to the body surface. The agents of the formulation can be in a single step, in separate steps or the agents can be applied in any combination thereof to allow for delivery of the active ingredient. Accordingly, the method of the present invention can include, in one embodiment, the steps of administering at least one penetration agent to the body surface; administering at least one basement membrane disruptor to the body surface, wherein the basement membrane disruptor reversibly denatures the basement membrane; administering at least one vaso-modulator; and administering at least one active ingredient, wherein the formulation allows for penetration of the active ingredient to the dermis. Each of these agents are described herein. In one embodiment, the penetration agent, basement membrane, vaso-modulator, and active ingredient are applied sequentially, and in another method, they are applied in combination. The method can optionally further include applying an occlusive barrier to the body surface.

The present invention further includes systems or kit for transdermal delivery of an active ingredient to a mammal. The kit or system encompasses the agents described herein and include at least one penetration agent, at least one basement membrane disruptor that reversibly denatures the basement membrane; at least one vaso-modulator; and at least one active ingredient. The kit or system creates a formulation that allows for penetration of the active ingredient to the dermis. In the case of a kit, the present invention also includes a set of written instructions for use, by or on said mammal.

Advantageously, the transdermal delivery formulation of the present invention results in an expanded range of active ingredients that can be delivered through the skin. For example, by using the formulation of the present invention, more complex, higher molecular weight, and lower log-p active agents can be effectively delivered through the dermis. The inventive formulation addresses a difficult-to-penetrate skin layer, the basement membrane, and allows for the passage of the active pharmaceutical agents into the dermis and subsequent delivery into localized tissue or the blood stream. This delivery avoids side effects of orally delivered medications.

DETAILED DESCRIPTION OF THE INVENTION

A description of preferred embodiments of the invention follows.

The skin, being the barrier organ of the body, consists of various structural layers. The layers of skin, starting from the outside, include the stratum corneum, epidermis, basement membrane and the dermis. The basement membrane is a very dense protein layer that separates the living tissue of the skin (dermis) from the non-living skin layers (epidermis, stratum corneum). The basement membrane is one of the densest tissues in the human body. In the skin, it functions to not only prevent foreign particles from penetrating into living tissue (the dermis), but it also functions to prevent fluids and living tissue constituents from moving out of the dermis and into the epidermis. In fact, in addition to providing a barrier and separation function, the basement membrane structurally anchors the epidermis to the dermis.

Each layer is unique and designed to either limit the rate of penetration of a foreign matter or completely block its penetration. The present invention utilizes the concept that layers of the skin, including the difficult-to-penetrate basement membrane, can be penetrated with certain chemical components. In particular, the present invention provides a novel transdermal delivery system that has a (e.g., one or more) basement membrane disruptor that allows for passage of the active ingredient through the basement membrane. In addition to the basement membrane disruptor, the transdermal delivery system of the present invention further includes a (e.g., one or more) penetration agent that allows for penetration of the stratum corneum, epidermis and a delivery package that encompasses a (e.g., one or more) vaso-modulator and an (e.g., one or more) active ingredient.

The basement membrane consists of two major protein layers. The first protein layer is called the basil lamina. The basil lamina is a dense structural protein layer with a thickness of approximately 20 nm-100 nm consisting of Type IV collagen. This layer has two component layers: lumina lucida and lumina densa. The second layer in the basement membrane consists of reticular connective tissue which is made up of collagen and connects to the basil lamina. Left unaltered, the basement membrane layers synergistically work to either prevent active pharmaceutical movement into the dermis or reduce the rate of flux to a level of sub-therapeutic drug flow. If the active pharmaceutical agent is not able to move into the dermis, it cannot move into deep local tissue or the blood stream for therapeutic benefit. Thus, using a basement membrane disruptor in the inventive delivery system allows for efficient permeation by the active drug compound through the basement membrane into the dermis and from there into local tissue or the blood stream for therapeutic purposes.

In accordance with illustrative embodiments of the present invention, the present invention relates to a transdermal drug delivery formulation that has at least three components. These component parts consist of: penetration agents, basement membrane disruptors and a delivery package. Each component can work by itself, or in combination with other agents/chemicals. The penetration agents function by allowing the delivery package and basement membrane disruptors to pass through the stratum corneum and epidermal skin layers and reach the basement membrane. The basement membrane disruptors function by temporarily or reversibly denaturing the basement membrane. In other words, the disrupter allows for basement membrane to denature and renature. During this action the basement membrane becomes permeable. This permeability then allows the delivery package to move into the dermis. The delivery package, which encompasses the active pharmaceutical agents and optionally other agents, is now, if desired, positioned to move out of the dermis and into either the blood stream or their intended therapeutic tissue.

FIG. 1 is a flow diagram, which outlines steps of method 100 for allowing an active agent to penetrate the skin, thereby entering the dermis, to deliver the active agent to localized tissue or the systemic circulation. The transdermal delivery formulation includes one or more penetration agents, one or more basement membrane disruptors and a delivery package which encompasses one or more active ingredients in combination with one or more vaso-modulator (e.g., a vasodilator or vasoconstrictor) (step 102. The formulation is applied to or within the skin in step 104, and once applied, steps 106, 108 and 110 occur. Once the formulation is applied to the skin, the penetration agent allows for passage of the basement membrane disruptor and the delivery package through the stratum corneum and the epidermis to the basement membrane in step 106. In step 108, the basement membrane disruptors induce reversible denaturing of the proteins which makes the basement membrane permeable and allows for passage of the delivery package through the basement membrane to the dermis. Once past the basement membrane, the vaso-modulator, in step 110, causes a fluid dynamic event to deliver the active ingredient to the local tissue or systemically. Optionally, the formulation can include excipients, penetration enhancers, lipids, or other substances. The formulation can also be a patch or a component of a patch or similar drug delivery device.

Penetration Agents

Penetration agents refers to one or more agents that function to penetrate through both the stratum corneum layer and the epidermal layer of the skin to the basement membrane. Penetration agents include one or more of the following: a solvent, a lipophilic agent, a hydrophilic agent, or a combination thereof. In an embodiment, the solvent used in the inventive transdermal delivery system can be one or more nonpolar solvents, one or more polar aprotic solvents (including dipolar aprotic solvents), one or more polar protic solvents, one or more limonenes, or combination thereof.

The penetration agent used in the present invention can be any combination of a solvent, a lipophilic agent, and/or a hydrophilic agent. A solvent can be used as the penetration agent alone or in combination with a lipophilic agent and/or a hydrophilic agent. In the case in which a solvent is not used, a combination of a lipophilic agent and/or a hydrophilic agent can be used to penetrate the stratum corneum layer and the epidermal layer of the skin. The penetration agents allow the basement membrane disruptor and delivery package to pass through the stratum corneum and epidermal layers and arrive at the basement membrane.

Polar solvents are those that have large dipole moments (aka "partial charges") and generally contain bonds between atoms with very different electronegativities, such as oxygen and hydrogen. Polarity can be measured using the dielectric constant or from directly measuring the dipole moment.

Non-polar solvents generally have bonds between atoms with similar electronegativities, such as carbon and hydrogen. Examples of non-polar solvents encompass carbon tetrachloride (CCl4), benzene (C6H6), diethyl ether (CH3CH2OCH2CH3), hexane (CH3(CH2)4CH3), and methylene chloride (CH2C12). An example of a non-polar, protic solvent further includes toluene.

Furthermore, protic solvents are those that contain a hydrogen atom linked to an oxygen (hydroxyl group) or to a nitrogen (amine group). Protic solvents are able to donate protons (H+). Conversely, aprotic solvents are those that do not donate hydrogen and cannot hydrogen bond with themselves but may accept hydrogen. Polar protic agents have high dielectric constants and high polarity. Examples of polar protic solvents: water (H—OH), methanol, isopropanol, acetic acid (CH3CO—OH) methanol (CH3-OH), ethanol (CH3CH2-OH), n-propanol (CH3CH2CH2-OH), n-butanol (CH3CH2CH2CH2-OH). Polar aprotic solvents exhibit intermediate dielectric constants, they are polar and are highly miscible in water. Examples of polar aprotic solvents are propylene carbonate. Examples of dipolar aprotic solvents include: acetone ((CH3)2C═O), ethyl acetate (CH3CO2CH2CH3), acetonitrile (CH3CN), and dimethylformamide ((CH3)2NC(O)H). In an embodiment, polar protic and/or polar aprotic solvents are preferred.

Limonenes used as a solvent in the present invention to penetrate the stratum corneum layer and the epidermis include D-limonene (citrus oils) or L-Limonenes (mint oils), and optionally together with a liquid hydrocarbon.

Additional examples of some penetration agents include individual fatty acids, fatty acid esters, polyols, amides, various anionic, cationic and nonionic surfactants such as but not limited to sodium laurate and sodium lauryl sulfate, phospholipids, cholesterol and cholesterol derivatives, m-pyrrole, dimethyl acetamide, limonene, sphingo lipids, ceramides, terpenes, alkanones, menthol, various organic acids, such as but not limited to salicylic acid, citric and succininc acid, prostaglandins, decyl-methyl sulfoxide, sulfoxide alcohols, plant extract oils. Suitable fatty acids include without limitation: linoleic acids, linolenic acids, oleic acids, stearic acids, and myristic acids. Phospholipids include without limitation: phosphatidylcholine, phosphatidylethanolamine, and phosphatidylserine. Plant extract oils include, but are not limited to, oils of peanut, grape seed, hemp, borage, tea tree, winter green, lemon, olive, sunflower, soy-bean, eucalyptus, monoi and macadamia. The plant extract oil can be mixed with an alcohol such as ethyl alcohol, isopropyl alcohol, and methyl alcohol. Penetration agents can also include vitamins for example like vitamin E, C or D.

Some penetration agents are commercially available from Fisher Scientific (Pittsburgh Pennsylvania, USA), Spectrum Chemical MFG Corp (New Brunswick, New Jersey, USA), or BASF (Florham Park New Jersey, USA). Penetration agents now known, or developed in the future, can be used in the compositions and methods of the inventive transdermal delivery system so long as the penetration agents allow for penetration of the basement membrane disruptor and delivery package through the stratum corneum layer and/or epidermal layer.

In an embodiment, the penetration agent can be included in the formulation in sufficient concentration and in effective amounts to allow for penetration through both the stratum corneum layer and/or the epidermal layer of the skin to the basement membrane. In an embodiment, a pharmaceutical transdermal formulation includes a concentration of penetration agents from about 1% w/w to about 60% w/w (e.g., 1, 5, 10, 15, 20, 25, 30, 35, 40, 45, 50, 55, 60% w/w).

Basement Membrane Disruptors

The transdermal delivery system and methods of the present invention utilize one or more basement membrane disruptors. They are agents that cause the basement membrane to become permeable. A basement membrane disruptor can be used by itself or in combination with others. By using these disruptors in the transdermal formulation and having the penetration agents move them to the basement membrane, the proteins in the basement membrane will be reversibly denatured. This denaturing process disrupts the quaternary, tertiary and/or secondary structures of the protein. Disrupting these structures will reversibly and temporarily alter the shape and confirmation of the protein allowing for permeability through the basement membrane and therefore allow for penetration of the delivery package of the transdermal delivery system.

Examples of basement membrane disruptor agents include one or more chaotropic agents or one or more other agents that allow for denaturing or permeability of the basement membrane proteins, or a combination thereof. Chaotropic agents are agents that disrupt the hydrogen bonding network between water molecules. Examples of a basement membrane disruptors include guanidine hydrochloride, a guanidine salt, guanidine analogs, guanidine conjugates or any combination thereof. An analog, as used herein, is a compound that has similar structural, physical, chemical, biochemical, functional, or pharmacological properties to that of guanidine, and is able to reversibly denature the basement membrane.

In an embodiment, the basement membrane disruptor can be included in the formulation in sufficient concentration (and therefore at sufficient activity) to create a condition of reversible denaturing of the proteins in the basement membrane. In an embodiment, a pharmaceutical transdermal formulation includes a concentration of basement permeation disruptors from about 0.2% w/w to about 10% w/w (e.g., 0.2, 0.3, 0.4, 0.5, 0.6, 0.7, 0.8, 0.9, 1, 1.2, 1.4, 1.6, 1.8, 2.0, 2.2, 2.4, 2.6, 2.8, 3.0, 3.5, 4.0, 4.5, 5.0, 5.5, 6.0, 6.5, 7.0, 7.5, 8.0, 8.5, 9.0, 9.5% w/w) of the formula. Concentrations at this level will cause only a temporary or reversible denaturing of the basement membrane proteins and not interfere with the primary structures. Once the disruptor has passed through basement membrane, they will begin to regain their original structure (renature). Such basement permeation disruptors are commercially available from Sigma Aldrich (St. Louis Missouri USA) or Thermo Fischer Scientific (Waltham Massachusetts USA). Basement membrane disruptors now known, or developed in the future, can be used in the formulations of the inventive transdermal delivery system so long as the disruptor causes permeability of the basement membrane or reversibly denatures the proteins of the basement membrane.

Delivery Package

The delivery package includes of the active pharmaceutical agents that are targeted to reach the living skin layer (dermis). The delivery package includes at least two types of compounds: the therapeutic drug or drugs having an "active agent" or "active ingredient" and a vaso-modulating agent.

Therapeutic Drugs

A "therapeutic drug," "active agent" or an "active ingredient" are interchangeable and refers to any component of a formulation that provides pharmacological activity or other direct effect in the diagnosis, cure, mitigation, treatment, amelioration, or prevention of disease, condition or disorder. Examples of active ingredients that are useful in the topically applied pharmaceutical formulations and methods of the instant invention include antifungal agents; anti-inflammatory agents, such as non-steroidal anti-inflammatory drugs (NSAIDS) and steroidal anti-inflammatory drugs; antibiotics; antiviral agents; anti-neoplastic agents; astringents; anesthetics; systemic drugs; steroid hormones, such as estradiol and testosterone; cosmetic agents, such as skin moisturizers, protectants, and emollients; nutrients, such as vitamins; and ceramides, and other known to those skilled in the art (e.g., those ingredients listed by the U.S. Food and Drug Agency in "Approved Drug Products with Therapeutic Equivalence Evaluations (Orange Book)", available at: http://www.fda.gov/Drugs/InformationOnDrugs/ucm129662.htm that are judged suitable by those skilled in the art), the entire teaches are hereby incorporated by reference.

Specific examples of active ingredients include acetaminophen, acetohydoxamic acid, acetophenazine, acyclovir, albuterol, allopurinol, amiloride, amoxicillin, amphetamine, ampicillin, antisense polymers, atenolol, baclofen, beclomethasone, benfotiamine, betamethasone, budesonide, bumetanide, butorphanol, carbamazepine, carphenazine, celacoxhib, cefuroxime, cephradine, chloramphenicol, chlorothiazide, chlorzoxazone, cinoxacin, clorazepate, cloxacillin, cyclacillin, dapsone, dicloxacillin, diethylstilbestrol, dopamine, doxorubicin, erythropoietin, estradiol, fenoprofen, gabapentin, human growth hormone, hydralazine, hydrochlorothiazide, ibuprofen, indomethacin, insulin, isoproterenol, ketoprofen, levodopa, levothyroxine, meclofenamate, melphalan, metformin methyl salicylate, metronidazole, minoxidil, morphine, nadolol, nalidixic acid, naproxen, nomifensine, norfloxacin, oxaprozin, oxycontin, paramethasone, peptide fragments, perphenazine, phenylpropanolamine, pregabalin, probenecid, quinethazone, ritodrine, scopolamine, serotonin, sildenafil, tadalafil, terbutaline, terfenadine, tocainide, terbinafine, triamterene, trimethoprim, valacyclovir and any derivatives of these and combinations of the foregoing. The active ingredient can also be a sirtuin inhibitors such as nicotinamide, AIII, coumarin, sirtinol, alpha-NAD, carbamido-NAD, trichostatin A, suramin sodium, apicidin, BML-210, BML-266, depudecin, HC Toxin, ITSA1, nullscript, phenylbutyrate, sodium, scriptaid, splitomicin, or suberoyl bis-hydroxamic acid. Further, the active ingredient can be sirtuin activators such as resveratrol, isonicotinamide, butein, or luteolin. In addition, active ingredients can also be compounds extracted from plants including hemp and cannabis including compounds like CBD, THC, terpenes etc. Therapeutic drug or active ingredients now known, or developed in the future, can be used in the compositions and methods of the inventive transdermal delivery system.

In some embodiments of the invention, the active ingredient comprises a biological agent. Examples of biological agents include peptides, small proteins and protein fragments; antibody fragments; small nucleic acids and nucleic acid fragments such as aptamers and siRNA; or combinations of these.

In an embodiment, the active ingredient can be included in the formulation in sufficient concentration and in effective amounts to confer the desired effect of the active ingredient. The actual effective amounts of the active agent/ingredient or drug can vary according to the specific composition being utilized, the age, weight and condition of the patient. Dosages for a particular individual patient can be determined by one of ordinary skill in the art using conventional considerations, (e.g. by means of an appropriate, conventional pharmacological protocol). In an aspect, dosing will also depend on the therapeutic effect to be achieved for the disease state. In general, the amount of active ingredient present in the inventive formulation ranges from about 0.001% w/w to about 30% w/w (e.g., 0.001, 0.005, 0.01, 0.05, 0.1, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 15, 20, 25, 30%/w).

A Vaso-Modulating Agent

A "vaso-modulating agent" or "vasoactive agent" refer to either a vasodilator or a vasoconstrictor component of a formulation, and includes pro-drugs of such components. In other words, "vaso-modulating agent" or "vasoactive agent" are agents that create intra-dermis fluid dynamic events.

The vaso-modulating agent is the active chemical agent designed to create a fluid dynamic event in the dermis in order to move the therapeutic drug from the skin into either the blood stream, lymphatic system or deep into local tissue so that the drug can impart therapeutic benefit. In an embodiment in which the target is the skin itself, then a vaso-modulating agent may not be needed and is optional, or a vasoconstrictor can be used to keep the active agent local. In an embodiment in which therapy is attempting to increase blood flow into local tissue, then the vaso-modulating agent acts also as the therapeutic drug. In another embodiment, a vasodilating agent can be included in the formulation in sufficient concentration and in effective amounts to create a fluid dynamic event in the dermis in order to move the therapeutic drug from the skin into either the blood stream, lymphatic system or deep into local tissue. In an embodiment, a pharmaceutical transdermal formulation includes a concentration of vaso-modulating agent from about 0.005% w/w to about 15% w/w (e.g., 0.005, 0.01, 0.05, 0.1, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, or 15% w/w) of the formula.

The vascular modifying agent can be a vasodilator. The vasodilator can be in an amount that is effective to cause dilation of capillaries in the dermis, increased blood and fluid flow through the capillaries in the dermis, and/or increased permeation of fluid through the walls of blood vessels in the skin of the patient. The species of vasodilator can be chosen depending on the speed with which the active drug should move from the dermis and therefore affect the tissue being targeted. Aggressive vasodilators like tolazoline, sodium nitroprusside and papaverine can be used to quickly move the active drug from the dermis into the bloodstream. Mild vasodilators like arginine can be used to slowly release the drug from the dermis into the blood stream so that it can be predominately taken up by the localized tissue or provide release over an extended period of time. Vasodilators include, for example, amrinone, arginine, bamethan sulphate, bencyclane fumarate, benfurodil hemisuccinate, benzyl nicotinate, buflomedil hydrochloride, buphenine hydrochloride, butalamine hydrochloride, cetiedil citrate, ciclonicate, cinepazide maleate, cyclandelate, di isopropylammonium dichloroacetate, ethyl nicotinate, hepronicate, hexyl nicotinate, ifenprodil tartrate, inositol nicotinate, isoxsuprine hydrochloride, kallidinogenase, methyl nicotinate, naftidrofuryl oxalate, nicametate citrate, niceritrol, nicoboxil, nicofuranose, nicotinyl alcohol, nicotinyl alcohol tartrate, nitric oxide, nonivamide, oxpentifylline, papaverine, papaveroline, pentifylline, peroxynitrite, pinacidil, pipratecol, propentofyltine, raubasine, suloctidil, teasuprine, thymoxamine hydrochloride, tocopherol nicotinate, tolazoline, papaverine, xanthinol nicotinate, diazoxide, hydralazine, minoxidil, and sodium nitroprusside. Centrally acting agents include clonidine, quanaberz, and methyl dopa. Alpha adrenoceptor blocking agents include indoramin, phenoxybenzamine, phentolamine, and prazosin. PDE-5 inhibitors including sildenafil, tadalafil. Adrenergic neuron blocking agents include bedmidine, debrisoquine, and guanethidine. ACE inhibitors include benazepril, captopril, cilazapril, enalapril, fosinopril, lisinopril, perindopril, quinapril, and ramipril. Ganglion blocking agents include pentolinium and trimetaphan. Calcium channel blockers include amlodipine, diltiazem, felodipine, isradipine, nicardipine, nifedipine, nimodipine, and verapamil. Prostaglandins including: prostacyclin, thrombuxane A2, leukotrienes, PGA, PGA1, PGA2, PGE1, PGE2, PGD, PGG, and PGH. Angiotensin II analogs include saralasin. Other suitable vasodilators include nitroglycerin, labetalol, thrazide, isosorbide dinitrate, pentaerythritol tetranitrate, digitalis, hydralazine, diazoxide, and sodium nitroprusside, derivatives of these and combinations of the foregoing. Also, natural vasodilators can be used in the inventive formulation. Natural vasodilators include cinnamaldehyde, tea tree oil, eucalyptus, lemon, coriander, peppermint, helichrysum, cistus, cypress, lentisque, juniper berry, niaouli, ginger, rosemary, basil, sage, geranium and cumin. Vasodilators for use with the present invention are commercially available, for example, from Sigma Aldrich (St. Louis Missouri USA), BASF (Florham Park New Jersey, USA), or Hawaii-Pharm (Honolulu, Hawaii (USA). Vasodilators now known, or developed in the future, can be used in the compositions and methods of the inventive transdermal delivery system so long as the vasodilators creates a fluid dynamic event in the dermis to move the therapeutic drug from the skin into either the blood stream, lymphatic system or deep into local tissue.

In an embodiment, the vascular modifying agents can be vasoconstrictors in order to keep the active ingredient/active drug in the skin (e.g., at the dermis) to treat skin disorders or the like. A vasoconstrictor that can be used in the present invention includes an agent that narrows blood vessels in the dermis. A vasoconstrictor can be used in the instance when local dermal tissue is targeted. The vasoconstrictor allows the active ingredient to remain localized and reduces or eliminates release into systemic circulation. Examples of vasoconstrictors include adenosine triphosphate, amphetamine, antazoline, asymmetric dimethylarginine, cocaine, dopamine, endothelin, ephedrine, epinephrine, ergine, hydroxyamphetamine, isoproterenol, levonordefrin, metaraminol, methamphetamine, methoxamine, methylphenidate, neuropeptide Y, naphazoline, norepinephrine, oxymetazoline, phenylephrine, pseudoephedrine, tetrahydozoline, thromboxane, tramazoline, tyramine, derivatives of these and combinations of the foregoing. Such vasoconstrictors are commercially available, for example, from Spectrum Chemical MFG Corp (New Brunswick, New Jersey, USA), BASF (Florham Park New Jersey, USA), or Thermo Fischer Scientific (Waltham Massachusetts USA). Vasoconstrictors now known, or developed in the future, can be used in the compositions and methods of the inventive transdermal delivery system so long as the vasoconstrictors creates a fluid dynamic event in the dermis involving a narrowing of the blood vessels to keep the active ingredient in the dermis and prevent or reduce release of the active ingredient from the skin The vasoactive agent can be chosen to exert effects rapidly (e.g., within 10 minutes or less), over a longer period of time (e.g., over the course of an hour or more). The vasoactive agent can also be chosen to give a delayed release (e.g., release begins after 10 minutes). Multiple vasoactive agents can be combined to result in both rapid and longer-term effects on the skin.

The transdermal delivery system of the present invention can be a formulation having the agents described herein. A "formulation" is a preparation in which various chemical substances are combined with an active ingredient. As used herein, a formulation includes a composition of the invention in the form of an emulsion, ointment, cream, lotion, gel, salve or the like, for topical application or delivery of the drug to a patient. In some embodiments, as appropriate, a formulation is used in conjunction with a delivery system (such as a patch) impregnated with or containing a composition suitable for topical application. The term "patient" or "individual" refers to any animal, including mammals such as a human, non-human primate, mouse, rat, guinea pig, rabbit, pig, horse or dog.

The transdermal delivery system is applied topically to an individual. "Topical" application shall mean application of a formulation to body surfaces such as the skin or mucous membranes, for example the vagina, anus, throat, nose, eyes and ears. For purposes of applying a formula, topical application shall include application to the stratum corneum, microinjection to the epidermis (such as can be achieved with microneedles), or use of sonophoresis, iontophoresis or other permeation-enhancing methods, without piercing of the basement membrane and subsequent injection to the dermis or subcutaneous structures.

In general, the application of the topical/transdermal formulation of the components, e.g., the components of the penetration agent, basement membrane disruptor and delivery package, can occur simultaneously or sequentially in time. Thus, the term "co-administration" is used herein to mean that the components of the transdermal delivery system will be administered at times to achieve delivery of the active ingredient. In an embodiment, the formulation is applied in order to penetrate layers of the skin, starting from the outside layers and going inward. Accordingly, in an embodiment, the penetration agents are applied first, then the basement disruptors and subsequently or simultaneously the delivery package. In other embodiments, the methods of the present invention are not limited to the sequence in which the compounds are administered, so long as the delivery package penetrates through the outer layers of the skin to the dermis. A transpiration barrier can also be applied sequentially with respect to the other components one or more times.

In some embodiments, the functions of two or more penetration agents, basement membrane disruptors and/or vaso-modulators can be provided by a single compound. In other words, in an embodiment, a single compound can have more than one function, and act as a penetration agent, a basement membrane disruptor and/or a vaso-modulator.

In some embodiments the transdermal delivery formula may be used with a transpiration barrier or an occlusive barrier. A "transpiration barrier" shall mean a component such as a solid patch, a hydrophobic chemical component, or a self-assembling chemical component (including components that form gels) that is capable of preventing water loss from skin tissue due to transpiration when applied to the skin of a patient. An "occlusive barrier" can be used to apply the formula to the skin or other tissue (e.g., application device), to prevent against cross contamination of clothes or other individuals (e.g., barrier device), to allow for timed release or enhanced delivery (e.g., delivery device). In an embodiment, the occlusive barrier is in the form of a physical patch like material, a tegaderm like barrier material, or a transpirational barrier (silicone, vasoline etc).

In an embodiment, the method includes optionally applying a transpiration barrier. The transpiration barrier can be a water impermeable drug administration patch; for example, a sheet of water-resistant plastic with an adhesive layer or other attachment mechanism. The patch can be applied atop a formulation applied to the skin. Alternately, the patch can be impregnated with the formulation and applied to the skin to contact the vaso-modulator agent, active ingredient, the basement membrane or the penetration agent with the skin while forming the transpiration barrier. A water-impermeable wrap, glove, sock, mitten, or the like can also serve to create a physical barrier. Alternately, or in addition, the transpiration barrier can include a molecular (i.e., chemical) barrier; i.e., one that contains a plurality of molecules or particles that are at least initially unbonded and which dry on or embed in the skin to produce a moisture-resistant barrier. For example, the molecular barrier can include silicone, titanium oxide, polyvinyl alcohol and hydrogels. It should be noted that both a chemical barrier and a physical barrier can be used together or sequentially.

Figure 1:
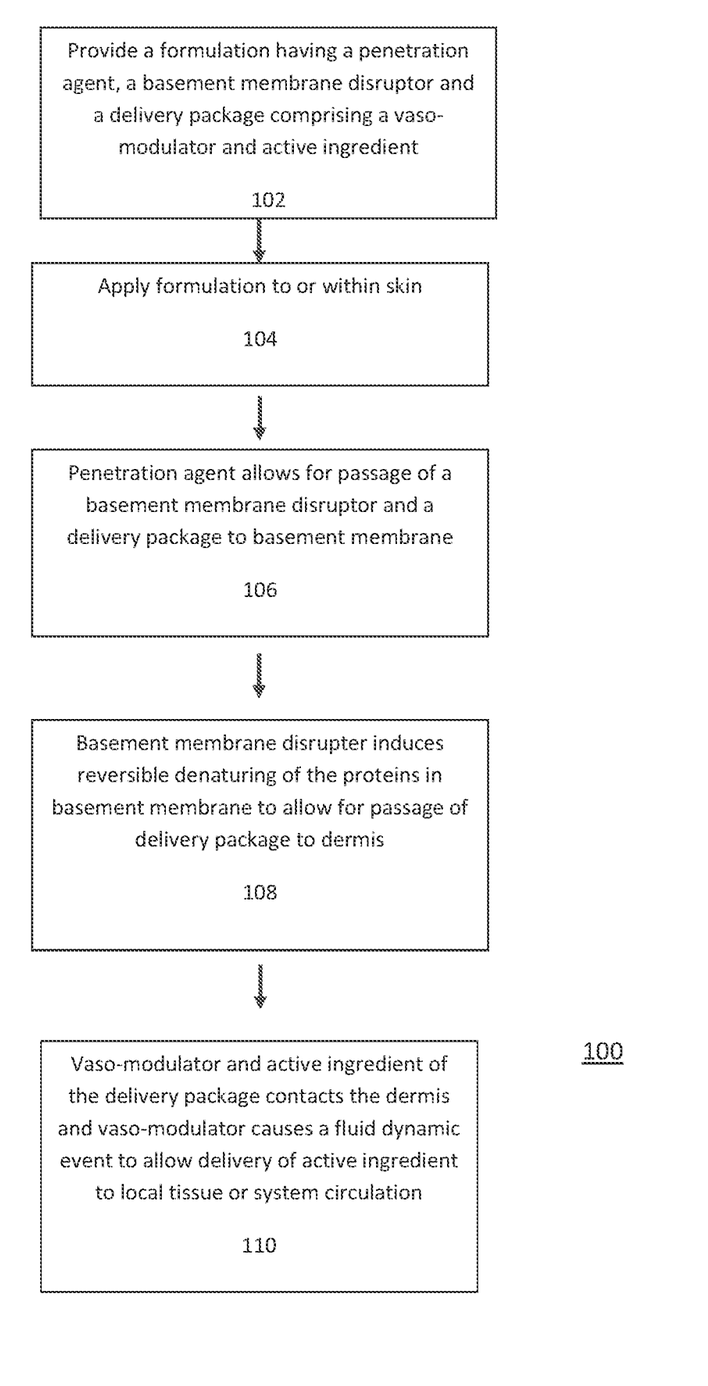
FIG. 1 is a flow diagram showing the steps of method 100 of the transdermal delivery system of the present invention.

The formulation can be applied to the skin; i.e., topically (step 104). For example, the formulation can be a cream, lotion, ointment, gel, or other substance suitable for topical application to the skin. Optionally, the skin can be mechanically worked to enhance the penetration of the active ingredient past the epidermis (e.g., into or through the basement membrane). For example, mechanical work can be used in the form of massaging, or sonophoresis. Mechanical working processes also include processes of cutting, ulceration, wound formation or piercing. For example, piercing the skin with microneedles (e.g., with a device having projections designed to pierce the stratum corneum without the substantial triggering of deeper pain receptors) can aid in the drug delivery process. Microneedles are disclosed, for example, in U.S. Pat. No. 6,611,707, issued on Aug. 26, 2003 to Prausnitz, which is incorporated herein by reference in its entirety. Sonophoresis (e.g., via ultrasound) can also be used to exert mechanical work and enhance penetration. Electrical work can also be employed; e.g., iontophoresis. The above list is an illustrative and not exhaustive list of working processes that can be employed in connection with embodiments of the present invention. Optionally, the formulation can be delivered into the skin. For example, the formulation can be injected into the epidermis with microneedles.

The formulation can also include excipients or carriers such as Stearyl Alcohol, Polysorbate 20, Caprylic/Capric Glyceride, Petrolatum, Beeswax, Lecithin, Dimethicone, Alkylmethyl Siloxane, Stearic Acid, Palmitic Acid, Lanolin, Linoleic Acid, Isopropyl Myristate, Stearyl Octanoate and Cetyl Octanoate, and Polysorbate 80.

Embodiments of the invention can be useful for medical conditions, diseases or disorders such as musculoskeletal diseases, vascular diseases, neurological diseases, viral, bacterial or parasitic diseases, blood disorders, skin diseases, autoimmune diseases, organ diseases, pain, and others. The number of diseases is numerous, but some examples include basal cell carcinomas, melanoma, cervical carcinomas, cervical condylomas, genital warts, herpetic lesions, diabetic neuropathy, chemotherapy-derived neuropathy, general neuropathy, benign prostatic hypertrophy, solid tumors, psoriasis, and eczema. In some embodiments, the active ingredient is a sirtuin inhibitor or sirtuin activator and the formulation is applied to the skin of a patient to treat one of these medical conditions. Where accessible, the formulation can be applied to a region of the skin or tissue associated with the medical condition.

In some embodiments of the invention, the formulation is cosmetically suitable in that it can be applied to the skin without detrimentally affecting the appearance of the skin.

In addition to application to the skin, the formulation can be applied to other exterior regions of the body including to the fingernails, toenails, ocular tissue, vagina, rectum (as a suppository), and other tissue surfaces containing an epithelial cell layer.

A formulation can be tested for its ability to increase circulation using laser Doppler velocimetry measurements. Such measurements are known in the art (see, e.g., Holloway G A Jr, Watkins D W., 1977, Laser Doppler measurement of cutaneous blood flow. J Invest Dermatol., September; 69(3):306-9). The test can be performed on participants after a 20-minute acclimatization period in a warm environment (room temperature 24° C.). For each subject, the blood flow response is measured with the non-invasive test before and after the application of the test formulation and at various intervals of time after the application until the blood flow has returned to a pre-application level. The measurement of skin blood flow can be evaluated using a Laser Doppler Perfusion Imager (LDPI Lisca 2.0, Lisca development AB, Linkoping, Sweden). This apparatus employs a 1 mW Helium-Neon laser beam of 633 nm wavelength, which sequentially scans the tested area. Typically, maximum number of measured spots is 4096 and the apparatus produces a color-coded image of the tissue perfusion distribution on a computer monitor. The data acquired from the instrument can be statistically analyzed with The Minitab statistical package (Minitab, State College, Pa.) for personal computers. For intra-group comparisons, the paired t-test can be used to compare changes between baseline and the maximal vasodilation. The test can be used for comparison between the two groups of patients. Changes in the microvascular blood flow can be expressed as the difference between the peak response and the baseline blood flow (e.g., in ml/min, laser-doppler velocimetry voltage readout, or other suitable units).

In some embodiments of the invention, application of the formulation can cause an increase in blood flow at or near the region of application. The increase can range from about 1% to greater than about 500%.

Animal models can be used to evaluate the effectiveness of a topically applied formulation in penetrating the skin tissue for either intradermal or transdermal systemic distribution of the active ingredient. Animal models that are preferred include pigs, guinea pigs, rabbit and mini-pigs. An example of the procedure used for such a study using guinea pigs is as follows: Male Hartley guinea pigs (250-300 g) are shaved on the back, and an area of 4×4 cm depilated with Nair® depilatory cream. After approximately 24 hours, 0.5 g of test compound in a topical formulation is applied to the 4×4 cm area and covered with an occlusive wrap. At 1, 2, 4, 8 and 24 hours after application, groups of >5 animals are anesthetized with isoflurane, the application area is swabbed with alcohol, blood is removed by cardiac stick, and the skin tissue of the application area is excised. One group of animals is anesthetized and blood and skin tissue are removed as vehicle control. Blood samples are processed to serum and analyzed for the presence of an active ingredient via HPLC. The skin below the area of compound application on each animal group is excised, weighed, homogenized in a mixture of acetonitrile and 0.1N HCl (50:50 v/v), centrifuged, and the extract analyzed for the presence of active ingredient via HPLC via HPLC. The amount of active ingredient in the blood and the amount of active ingredient in the skin tissue may be compared to give information about the pharmacokinetics of the active ingredient. For delivery to skin tissue (e.g., a skin tumor or lesion), a higher amount in the skin relative to the blood is more efficacious, whereas when the goal is systemic delivery of the active ingredient, a higher distribution in the blood is more efficacious.

The transdermal delivery system of the present invention is effective in delivering the active ingredient. In some embodiments, the inventive transdermal delivery system is as effective in delivering the active ingredient, as compared to traditional methods of administration such as oral administration. In the case of certain embodiments, the inventive transdermal delivery system delivers the active ingredient more effectively, as compared to its oral administration or other transdermal administrations (at least about 5, 10, 15, 20, 25, 30, 35, 40, 45, 50, 55, 60, 65, 70, 75, 80, 85, 90, 95, or 100% more effective).

In another embodiment, a kit or system is used for topical or transdermal delivery of an active ingredient to a patient. The kit includes one or more of the following: a penetration agent, a basement membrane disruptor and a delivery package comprising a vaso-modulator and active ingredient. The kit can also include a set of written instructions for use thereof according to one of the methods of topical or transdermal delivery described herein. The kit optionally includes an occlusive barrier.

In yet another embodiment, a kit is supplied to a compounder. The kit contains the components/agents described herein (e.g., a penetration agent, a basement membrane disruptor and a delivery package) and it allows the compound pharmacist to manufacture the formulation of the present invention.

In another embodiment, there is a method of manufacturing a medicament for transdermal administration. The method includes combining a penetration agent, a basement membrane disruptor and a delivery package comprising a vaso-modulator and active ingredient in sufficient amounts to cause permeation of the active ingredient to at least one affected region of a patient when applied to one of the skin and other exterior region of the patient.

EXEMPLIFICATION

Example 1

Part A

| Component | % w/w |
| --- | --- |
| Water | 71.5 |
| Carbomer 940 (Thickener) | 1 |
| Guanidine HCl (Basement Membrane Disrupter/Chaotropic Agent) | 0.5 |
| Glycerin (Humectant) | 2 |
| Caffeine (Active Ingredient) | 1 |
| Urea (Humectant) | 5 |
| Arginine HCl (Vaso-modulator/Vasodilator) | 0.5 |

Part B

| Component | |
| --- | --- |
| Oleic Acid (Emulsifier/Penetration Enhancer/Agent) | 3 |
| Glyceryl Monostearate (Emulsifier) | 3 |
| Stearyl Alcohol (Emollient/Viscosity Builder) | 3 |
| Cremophor RH-40 (Emulsifier/Solubilizer) | 2 |
| Arlacel 165 (Emulsifier) | 2 |

Part C

| Component | % w/w |
| --- | --- |
| Optiphen MIT Plus (Preservative) | 0.2 |
| Isopropanol (Solvent) | 5 |
| Triethanolamine (pH neutralizer) | 0.3 |

Procedure:
1. Add water into main vessel, turn on mixer. Slowly sprinkle Carbomer 940 into vessel while mixing. Mix until no visible lump and start to heat the vessel to 70 C.
2. Add rest ingredients in the Part A into the main vessel while keeping mixing and keep temperature at 70 C.
3. Add all ingredients in Part B into a separate vessel, heat to 70 C. Once it becomes clear at 70 C, add it into main vessel while mixing.
4. Mix 5 minutes at 70 C, then start to cool down the batch to room temperature.
5. Add all ingredients in Part C into a separate vessel, mix well and slowly add into main vessel at room temperature.
6. Mix for another 15-20 minutes until it's homogenous.

Example 2

Part A

| Component | % w/w |
| --- | --- |
| Water | 72.3 |
| Carbomer 940 (Thickener) | 0.7 |
| Guanidine HCl (Basement Membrane Disrupter/Chaotropic Agent) | 1 |
| Glycerin (Humectant) | 2 |
| Urea (Humectant) | 5 |
| Arginine HCl (Vaso-modulator/Vasodilator) | 0.5 |

Part B

| Component | % w/w |
| --- | --- |
| Oleic Acid (Emulsifier/Penetration Enhancer/Agent) | 3 |
| Glyceryl Monostearate (Emulsifier) | 3 |
| Stearyl Alcohol(Emollient/Viscosity Builder) | 3 |
| Cremophor RH-40 (Emulsifier/Solubilizer) | 2 |
| Arlacel 165 (Emulsifier) | 2 |

Part C

| Component | % w/w |
| --- | --- |
| Oleic Acid(Emulsifier/Penetration Enhancer/Agent) | 2 |
| Tolnaftate (Active Ingredient) | 1 |

Part D

| Component | % w/w |
| --- | --- |
| Optiphen MIT Plus (Preservative) | 0.2 |
| Dimethyl Sulfoxide (Solvent) | 2 |
| Triethanolamine (pH neutralizer) | 0.3 |

Procedure:
1. Add water into main vessel, turn on mixer. Slowly sprinkle Carbomer 940 into vessel while mixing. Mix until no visible lump and start to heat the vessel to 70 C.
2. Add rest ingredients in the Part A into the main vessel while keeping mixing and keep temperature at 70 C.
3. Add all ingredients in Part B into a separate vessel, heat to 70 C. Once it becomes clear at 70 C, add it into main vessel while mixing.
4. Mix 5 minutes at 70 C, then start to cool down the batch to room temperature.
5. Mix all ingredients together in Part C in a separate vessel, then add it into main vessel at room temperature.
6. Add all ingredients in Part D into a separate vessel, mix well and slowly add into main vessel at room temperature.
7. Mix for another 15-20 minutes until it's homogenous.

The terms about, approximately, substantially, and their equivalents may be understood to include their ordinary or customary meaning. In addition, if not defined throughout the specification for the specific usage, these terms can be generally understood to represent values about but not equal to a specified value. For example, 1%, 0.9%, 0.8%, 0.7%, 0.6%, 0.5%, 0.4%, 0.3%, 0.2%, 0.1%, or 0.09% of a specified value.

The terms, "comprise," "include," "having" and/or plural forms of each are open ended and include the listed items and can include additional items that are not listed. The phrase "And/or" is open ended and includes one or more of the listed items and combinations of the listed items.

The relevant teachings of all the references, patents and/or patent applications cited herein are incorporated herein by reference in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. A formulation for transdermal delivery of an active ingredient to a mammal, said mammal having a body surface that comprises a stratum corneum, an epidermis, a basement membrane, and a dermis; the formulation comprises
   a) at least one penetration agent comprising a solvent, a lipophilic agent, a hydrophilic agent, or a combination thereof;
   b) at least one basement membrane disruptor, wherein the basement membrane disruptor is present in an amount ranging from about 0.2% w/w and about 10% w/w;
   c) at least one vaso-modulator; and
   d) at least one active ingredient;
   wherein the formulation allows for penetration of the active ingredient to the dermis.

2. The formulation of claim 1, wherein the body surface comprises skin, mucosal membranes and nail surfaces.

3. The formulation of claim 1, wherein the body surface comprises skin, vaginal mucosa, anal mucosa, throat mucosa, nasal mucosa, ocular tissue, fingernail surface, or toe nail surface.

4. The formulation of claim 1, wherein the penetration agent is present in an amount ranging from about 1% w/w and about 60% w/w.

5. The formulation of claim 1, wherein the penetration agent allows the basement membrane disruptor, the vaso-modulator, and the active ingredient to pass through the stratum corneum layer and the epidermis.

6. The formulation of claim 1, wherein the penetration agent comprises the solvent, wherein the solvent is selected from the group consisting of: one or more nonpolar solvents, one or more polar aprotic solvents, one or more polar protic solvents, one or more limonenes, and a combination thereof.

7. The formulation of claim 6, wherein the penetration agent comprises one or more nonpolar solvents is selected from the group consisting of: carbon tetrachloride, benzene, diethyl ether, hexane, methylene chloride, toluene and a combination thereof.

8. The formulation of claim 6, wherein the penetration agent comprises one or more polar aprotic solvents is selected from the group consisting of: propylene carbonate, acetone, ethyl acetate, acetonitrile, dimethylformamide, and a combination thereof.

9. The formulation of claim 6, wherein the penetration agent comprises one or more polar protic solvents is selected from the group consisting of: water, methanol, isopropanol, acetic acid, methanol, ethanol, n-propanol, n-butanol and a combination thereof.

10. The formulation of claim 6, wherein the penetration agent comprises one or more limonenes is selected from the group consisting of: D-limonene, L-Limonenes and a combination thereof.

11. The formulation of claim 1, wherein the basement membrane disruptor denatures one or more molecules of the basement membrane to allow for passage of the active ingredient, and wherein the one or more molecules of the basement membrane renature once the active ingredient is delivered to the dermis.

12. The formulation of claim 1, wherein the basement membrane disruptor allows the vaso-modulator and the active ingredient pass through the basement membrane.

13. The formulation of claim 1, wherein the basement membrane disruptor comprises one or more chaotropic agents.

14. The formulation of claim 1, wherein basement membrane disruptor is selected from the group consisting of: guanidine hydrochloride, a guanidine salt, guanidine analogs, guanidine conjugates; and a combination thereof.

15. The formulation of claim 1, wherein the vaso-modulator is present in an amount ranging from about 0.005% w/w and about 15% w/w.

16. The formulation of claim 1, wherein the vaso-modulator comprises a vasodilator or vasoconstrictor.

17. The formulation of claim 16, wherein the vasodilator allows for the active ingredient to be delivered systemically or to local tissue.

18. The formulation of claim 16, wherein the vasodilator is selected from the group consisting of: amrinone, arginine, bamethan sulphate, bencyclane fumarate, benfurodil hemisuccinate, benzyl nicotinate, buflomedil hydrochloride, buphenine hydrochloride, butalamine hydrochloride, cetiedil citrate, ciclonicate, cinepazide maleate, cyclandelate, di isopropylammonium dichloroacetate, ethyl nicotinate, hepronicate, hexyl nicotinate, ifenprodil tartrate, inositol nicotinate, isoxsuprine hydrochloride, kallidinogenase, methyl nicotinate, naftidrofuryl oxalate, nicametate citrate, niceritrol, nicoboxil, nicofuranose, nicotinyl alcohol, nicotinyl alcohol tartrate, nitric oxide, nonivamide, oxpentifylline, papaverine, papaveroline, pentifylline, peroxynitrite, pinacidil, pipratecol, propentofyltine, raubasine, suloctidil, teasuprine, thymoxamine hydrochloride, tocopherol nicotinate, tolazoline, papaverine, xanthinol nicotinate, diazoxide, hydralazine, minoxidil, and sodium nitroprusside, clonidine, quanaberz, methyl dopa, alpha adrenoceptor, indoramin, phenoxybenzamine, phentolamine, prazosin, PDE-5 inhibitors, sildenafil, tadalafil, adrenergic neuron blocking agents, bedmidine, debrisoquine, guanethidine, ACE inhibitors, benazepril, captopril, cilazapril, enalapril, fosinopril, lisinopril, perindopril, quinapril, ramipril, ganglion blocking agents, pentolinium, trimetaphan, calcium channel blockers, amlodipine, diltiazem, felodipine, isradipine, nicardipine, nifedipine, nimodipine, verapamil, prostaglandins, prostacyclin, thrombuxane A2, leukotrienes, PGA, PGA1, PGA2, PGE1, PGE2, PGD, PGG, PGH, angiotensin II analogs, saralasin, nitroglycerin, labetalol, thrazide, isosorbide dinitrate, pentaerythritol tetranitrate, digitalis, hydralazine, diazoxide, sodium nitroprusside, and a combination thereof.

19. The formulation of claim 16, wherein the vasoconstrictor allows for the active ingredient to be delivered to the dermis.

20. The formulation of claim 16, wherein the vasoconstrictor is selected from the group consisting of: adenosine triphosphate, amphetamine, antazoline, asymmetric dimethylarginine, cocaine, dopamine, endothelin, ephedrine, epinephrine, ergine, hydroxyamphetamine, isoproterenol, levonordefrin, metaraminol, methamphetamine, methoxamine, methylphenidate, neuropeptide Y, naphazoline, norepinephrine, oxymetazoline, phenylephrine, pseudoephedrine, tetrahydozoline, thromboxane, tramazoline, tyramine, and a combination thereof.

21. The formulation of claim 1, wherein the active ingredient is present in an amount ranging from about 0.001% w/w and about 30% w/w.

22. The formulation of claim 1, wherein the active ingredient is selected from the group consisting of: acetaminophen, acetohydoxamic acid, acetophenazine, acyclovir, albuterol, allopurinol, amiloride, amoxicillin, amphetamine, ampicillin, antisense polymers, atenolol, baclofen, beclomethasone, benfotiamine, betamethasone, budesonide, bumetanide, butorphanol, carbamazepine, carphenazine, celacoxhib, cefuroxime, cephradine, chloramphenicol, chlorothiazide, chlorzoxazone, cinoxacin, clorazepate, cloxacillin, cyclacillin, dapsone, dicloxacillin, diethylstilbestrol, dopamine, doxorubicin, erythropoietin, estradiol, fenoprofen, gabapentin, human growth hormone, hydralazine, hydrochlorothiazide, ibuprofen, indomethacin, insulin, isoproterenol, ketoprofen, levodopa, levothyroxine, meclofenamate, melphalan, metformin methyl salicylate, metronidazole, minoxidil, morphine, nadolol, nalidixic acid, naproxen, nomifensine, norfloxacin, oxaprozin, oxycontin, paramethasone, peptide fragments, perphenazine, phenylpropanolamine, pregabalin, probenecid, quinethazone, ritodrine, scopolamine, serotonin, sildenafil, tadalafil, terbutaline, terfenadine, tocainide, terbinafine, triamterene, riamterine, a sirtuin inhibitor, nicotinamide, AIII, coumarin, sirtinol, alpha-NAD, carbamido-NAD, trichostatin A, suramin sodium, apicidin, BML-210, BML-266, depudecin, HC Toxin, ITSA1, nullscript, phenylbutyrate, sodium, scriptaid, splitomicin, suberoyl bis-hydroxamic acid, a sirtuin activators, resveratrol, isonicotinamide, butein, luteolin, plant extract, and a combination thereof.

23. The formulation of claim 1, further comprising a transpiration barrier, wherein the transpiration barrier includes at least one of a chemical barrier or a physical barrier.

24. A method for transdermal delivery of a formulation having an active ingredient to a mammal, said mammal having a body surface that comprises a stratum corneum, an epidermis, a basement membrane, and a dermis; the method comprises:
   a) applying the formulation to the body surface, wherein formulation comprises:
      i) at least one penetration agent comprising a solvent, a lipophilic agent, a hydrophilic agent, or a combination thereof;
      ii) at least one basement membrane disruptor, wherein the basement membrane disruptor is present in an amount ranging from about 0.2% w/w and about 10% w/w;
      iii) at least one vaso-modulator; and
      iv) at least one active ingredient;
   wherein the formulation allows for penetration of the active ingredient to the dermis.

25. A method for transdermal delivery of a formulation having an active ingredient to a mammal, said mammal having a body surface that comprises a stratum corneum, an epidermis, a basement membrane, and a dermis; the method comprises:
   a) administering at least one penetration agent to the body surface, wherein the penetration agent comprises a solvent, a lipophilic agent, a hydrophilic agent, or a combination thereof;
   b) administering at least one basement membrane disruptor to the body surface, wherein the basement membrane disruptor is present in an amount ranging from about 0.2% w/w and about 10% w/w;
   c) administering at least one vaso-modulator; and
   d) administering at least one active ingredient;
   wherein the formulation allows for penetration of the active ingredient to the dermis.

26. The method of claim 25, wherein the penetration agent, basement membrane, vaso-modulator, and active ingredient are applied sequentially.

27. The method of claim 25, wherein the penetration agent, basement membrane, vaso-modulator, and active ingredient are applied together.

28. The method of claim 25, further comprising applying an occlusive barrier to the body surface.

29. A kit for transdermal delivery of an active ingredient to a mammal, said mammal having a body surface that comprises a stratum corneum, an epidermis, a basement membrane, and a dermis; the kit comprises
   a) at least one penetration agent comprising a solvent, a lipophilic agent, a hydrophilic agent, or a combination thereof;
   b) at least one basement membrane disruptor, wherein the basement membrane disruptor is present in an amount ranging from about 0.2% w/w and about 10% w/w;
   c) at least one vaso-modulator; and
   d) at least one active ingredient;
   wherein the kit creates a formulation that allows for penetration of the active ingredient to the dermis.

30. The kit of claim 29, further comprising a set of written instructions for use, by or on said mammal.

* * * * *